United States Patent [19]

Riley et al.

[11] Patent Number: 5,506,345
[45] Date of Patent: Apr. 9, 1996

[54] METAL COMPLEXES FOR HYPOXIC CELLS

[75] Inventors: Anthony L. Riley, Amersham; James D. Kelly, Marlow, both of United Kingdom

[73] Assignee: Amersham International plc, United Kingdom

[21] Appl. No.: 280,108

[22] Filed: Jul. 25, 1994

Related U.S. Application Data

[62] Division of Ser. No. 899,312, Jun. 16, 1992, Pat. No. 5,387,692.

[30] Foreign Application Priority Data

Jun. 21, 1991 [GB] United Kingdom ............... 9113487

[51] Int. Cl.[6] .................. C07F 13/00; C07F 5/06; C07F 9/00; C07D 233/91
[52] U.S. Cl. .................. 534/14; 534/10; 548/106; 548/312.1; 548/327.5; 552/294; 556/37
[58] Field of Search ........................... 548/327.5

[56] References Cited

U.S. PATENT DOCUMENTS

| 2,545,421 | 3/1951 | Anish et al. | 548/312.1 X |
| 2,704,755 | 3/1955 | Kendall et al. | 548/312.1 X |
| 3,576,639 | 4/1971 | Jenkins | 548/312.1 X |
| 3,641,047 | 2/1972 | Beaman et al. | 548/327.5 |
| 4,550,175 | 10/1985 | Mixich et al. | 548/312.1 X |
| 5,036,096 | 7/1991 | Suto | 548/327.5 X |
| 5,110,826 | 5/1992 | Hori et al. | 548/327.5 X |
| 5,217,986 | 6/1993 | Pomponi et al. | 548/327.5 |

FOREIGN PATENT DOCUMENTS

| 61290/90 | 3/1991 | Australia | 548/106 |
| 0123504 | 10/1984 | European Pat. Off. | 548/106 |
| 0188256 | 7/1986 | European Pat. Off. | 548/106 |
| 0294847 | 12/1988 | European Pat. Off. | 548/106 |
| 0302416 | 2/1989 | European Pat. Off. | 548/106 |
| 0319329 | 6/1989 | European Pat. Off. | 548/106 |
| 0417870 | 3/1991 | European Pat. Off. | 548/106 |
| 2331549 | 6/1977 | France | 548/106 |
| 1521930 | 8/1978 | United Kingdom | 548/106 |
| 1521926 | 8/1978 | United Kingdom | 548/106 |
| 2213150 | 8/1989 | United Kingdom | 548/327.5 |

OTHER PUBLICATIONS

*Journal of Medicinal Chemistry*, 33(9), 2603–2610 (Sep. 1990), Jenkins et al.

*Primary Examiner*—Floyd D. Higel
*Attorney, Agent, or Firm*—Wenderoth, Lind & Ponack

[57] ABSTRACT

Agents for the diagnosis or treatment of hypoxic cells comprise a bioreductive moiety such as 2-nitroimidazole, and a metal chelating moiety which is a bis-amine oxime of which a carbon atom adjacent a nitrogen atom is linked to the bioreductive moiety. A chelated metal atom or ion preferably Technetium-99m. The agent diffuses into cells where the 2-nitroimidazole is reduced thus trapping the chelated metal in the cell.

9 Claims, No Drawings

METAL COMPLEXES FOR HYPOXIC CELLS

This is a Rule 60 divisional application of Ser. No. 07/899,312, filed Jun. 16, 1992, now U.S. Pat. No. 5,387,692.

It is known that certain molecules, known as bioreductive moieties, are capable of diffusing into and becoming immobilized in hypoxic cells. (See Mason, P. "Free Radicals in Biology" Academic Press 1982). Thus for example nitroimidazoles, and in particular, misonidazole (3-methoxy-1-(2-nitromidazol-1-yl)propan-2-ol) are used against anaerobic bacteria and as radiosensitising agents in hypoxic tumors. It is known that anaerobic metabolism leads to free radical formation and subsequent covalent binding of the nitroimidazole (or degradation product) within the hypoxic cell. In the presence of oxygen (aerobic cells), re-oxidation of the free radicals occurs continuously in a 'futile cycle'. Thus it is only under anaerobic conditions that the free radicals can exist long enough for combination with cellular components to occur, i.e. trapping in hypoxic tumors or in ischaemic, but viable myocardium.

Advantage has been taken of this property to devise labelled versions of misonidazole for diagnosis of hypoxia. The following references describe misonidazole and analogues labelled with the non-metallic species $^{18}F$, $^{3}H$, $^{125}I$, $^{131}I$, $^{77}Br$ and $^{75}Br$:

Hwang et al., Appl. Radiat. Isot., Vol. 40, No. 2, pp 112–128, 1989.

Mercer, J. R. et al., 7th Int. Symp. Radiopharm. Chem., pp. 107–108, Groningen, 1988.

Grierson, J. R. et al., J. Nucl. Med., 30, pp. 343–350, 1989.

Martin, G. V. et al., Circulation Res., 67, 1, pp. 240–244, 1990.

Grunbaum, Z. et al., J. Nucl. Med., 28, 1, pp. 68–75, 1987.

Chelated metal atoms may, in certain circumstances, be incorporated into bioreductive molecules without destroying the ability of the bioreductive molecules to discriminate between oxic and hypoxic cells. Radioactive metals can be used. Such agents offer advantages, over those discussed in the above references, of cost, availability and convenience.

EP 0 417 870 A2 describes compounds of the general formula $$(CR^1R^7B)-NR^3-CH_2-(CR^5R^6A)-CH_2-NR^4-(CR^2R^8 B^1) Y$$

where B may be a substituted nitrosomethyl group, A may comprise misonidazole, and $R^1$ to $R^8$ are as defined. These compounds are said to form complexes with radioactive metal ions which are suitable for diagnosis and tumor therapy. No compound is described in which B is nitrosomethyl or substituted nitrosomethyl and A comprises misonidazole or indeed other bioreductive moiety.

In one aspect the invention provides a ligand comprising at least one bioreductive moiety linked to a metal chelating moiety, wherein the metal chelating moiety is a bis-amine oxime of which a carbon atom adjacent a nitrogen atom is linked to the bioreductive moiety.

In another aspect the invention provides an agent for the diagnosis of hypoxia or for therapy of hypoxic tumors, comprising a ligand as defined and a metal atom chelated by the metal chelating moiety. In many cases, the agent can be visualized as having the structure Q-A-L-M or (Q-A)$_2$-L-M where Q is the bioreductive moiety, A is a linking group, L is the metal chelating moiety and M is the metal atom.

In these compounds, the bioreductive moiety may be any which has the ability to cause the agent to become trapped in hypoxic cells, for example those discussed in the P. Mason reference above, including quinones and aromatic nitrocompounds. Preferred are benzotriazine-di-n-oxides, triazoles, nitroacridines, nitroimidazoles including particularly 2-nitroimidazole, and their substituted analogues such as misonidazole. Alkyl, acyl, chloro-, bromo-, hydroxyalkyl, alkoxyalkyl, aminoalkyl, and other substituents may improve the properties of these bioreductive molecules. Other references to bioreductive molecules include: J. H. Tocher et al., Free Rad. Res. Comms., Vol 10, Nos. 4–5, pp 295–302, 1990; Y. Nagao et al., Tetrahedron, Vol. 46, No. 9, pp 3211–3232, 1990; and W. A. Denny et al., J. Med. Chem., 1990, 33, 1288–1295.

Bis amine oximes are tetradentate metal chelators having the general structure

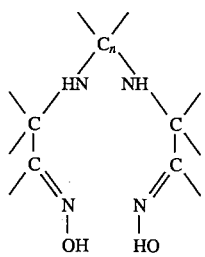

where n is 2 or 3, preferably 3. Usually these metal chelators have the structure

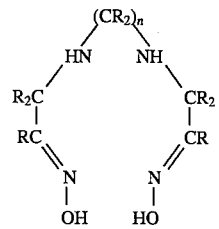

where the groups R may be the same or different and each is hydrogen; hydrocarbon such as alkyl, aryl or cycloalkyl which may be unsubstituted or substituted with a hydrophilic group such as amine, amide, hydroxyl, carboxylic acid or carboxylic ester; amine, amide, hydroxy, alkoxy, alkoxyalkyl, carboxylic acid or carboxylic acid ester. At least one group R adjacent a N atom is linked to a bioreductive moiety.

Bis amine oximes and their preparation are described in European Patent 123504B. The preparative techniques are readily adapted to introduce a reactive substituent attached to a carbon atom adjacent a nitrogen atom. The reactive substituent is provided to link the bis-amine oxime to the bioreductive moiety. It may for example be an aminoalkyl group. By contrast, it is less easy to synthesise a bis-amine oxime with a bioreactive moiety or a reactive substituent attached to the centre carbon atom of the propylene group. This is because such synthesis typically requires the use of a powerful reducing agent which may decompose the bioreactive moiety or reactive substituent.

The term metal atom is used herein to describe the metal species which may be present in a variety of oxidation states, or even associated with O, OH, Cl, etc., depending on its chemistry. The metal species chelated by the above ligand is preferably radioactive, although non-radioactive metals may be useful, for diagnosis e.g. as contrast agents in n.m.r. in some cases. Preferred radioactive metals include $^{99m}Tc$, $^{186}Re$, $^{188}Re$, $^{67}Cu$ and $^{107}Ag$.

In these agents, the metal chelating moiety L is joined to the bioreductive moiety Q by means of a linking group A.

Group A preferably comprises a chain from 1 to 12 atoms long, in which hetero atoms such as S, N and O are possible, as also are amide and ester linkages. The linking group A should not be so charged or so polar as to prevent diffusion of the complex through cell walls.

In vitro, the agent of this invention is capable of diffusing freely into oxic or hypoxic cells, but is preferentially trapped in hypoxic cells. In vivo where the agent is transported by the blood to hypoxic regions it diffuses through the cell walls. Once within the hypoxic cells it is a substrate for nitroreductases producing free radicals which, in the absence of $O_2$, become trapped, e.g. as a result of covalent bonding, within the cell. For these purposes, the agent has certain characteristics:

The agent as a whole is capable of diffusing into cells, for which purpose its partition coefficient is important. If the agent is too hydrophilic, it will not diffuse through cell walls. If it is too hydrophobic, it may be completely water-insoluble. The hydrophilic/lipophilic balance can quite readily be adjusted, e.g. by addition of hydrophilic or hydrophobic groups to the chelating moiety L or to the linking group A or to the bioreductive moiety Q, provided that the molecule should not be so charged or so polar as to prevent its diffusion through the cell walls.

Once in hypoxic cells, the agent is capable of being immobilized. For this purpose, the nitro or other bioreductive moiety should not be hindered by the chelating moiety.

The chelating moiety strongly binds the metal, and does not significantly release it in solution or in the bloodstream. Thus, the metal is introduced and becomes immobilized within the hypoxic cells.

Our agents have the advantage that they enter cells by passive diffusion rather than by active transport. Compounds which enter cells by active transport are likely to have their properties impaired by substitution with metal chelating moieties.

Our agents are expected to be useful for myocardial viability assessment, perhaps in conjunction with current myocardial perfusion imaging techniques; and for cerebral viability assessment. Because tumors are often hypoxic, the agents are expected to be useful for both diagnosis and treatment of hypoxic tumors.

Reference is directed to the following formulae which represent the structures of various compounds referred to in the following experimental section formulas I, II, III, IV, V, VI, VII, VIII, IX, X, XI, and XII:

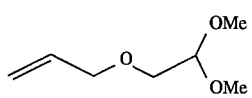

I

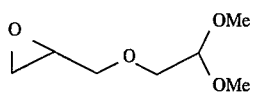

II

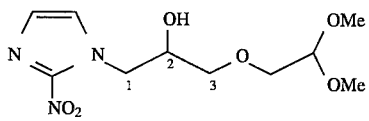

III

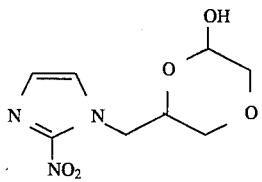

IV

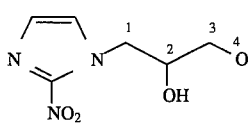

V

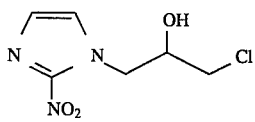

VI

-continued

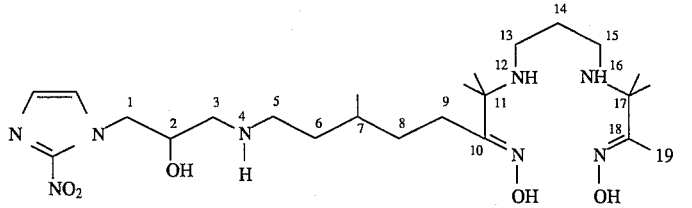

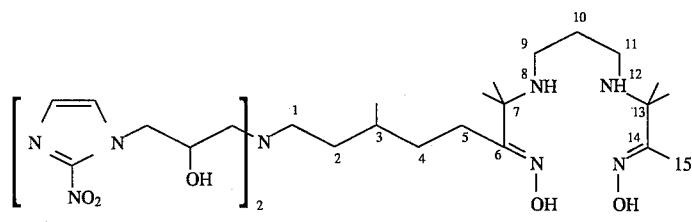

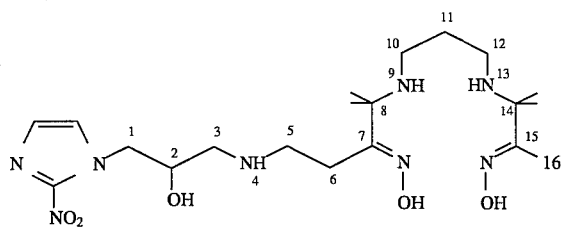

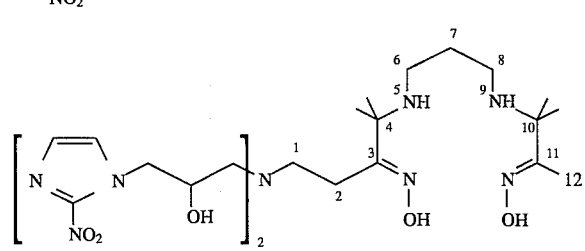

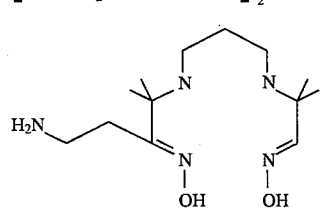

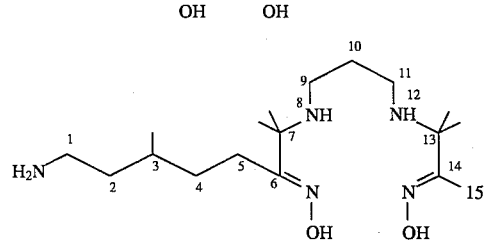

These structures include five ligands according to the invention as follows:

V
VII
VIII
IX
X

In the following experimental section, Examples 1 to 5 describe the preparation and characterization of the five ligands. Example 6 describes the labelling of them with technetium-99m to give agents according to the invention. In Example 7, these agents are tested in Chinese hamster fibroblasts in suspension in vitro.

VII

VIII

IX

X

XI

XII

EXAMPLES 1 TO 5

Synthesis 2-hydroxy-1-(2-nitro-1-imidazolyl)-7,15,19 -triaza-4-oxa-10,14,14,20,20-pentamethyldocosane-13,21-dione dioxime V.

Synthesis of 2-allyloxyacetaldehyde dimethyl acetal (I)

Allyl alcohol (obtained from Aldrich, 36 g) dissolved in dry tetrahydrofuran (Aldrich, 400 ml) was stirred with hexane-washed sodium metal (13.76 g). Bromoacetaldehyde dimethyl acetal (Aldrich, 71.0 g) was added and the solution was heated under reflux for a period of 18 hours. The solution was cooled and washed with sodium hydroxide solution (300 ml, 0.5M). The aqueous layer was washed with ethyl acetate, the organic phases were then combined, washed with brine and dried over anhydrous magnesium sulphate. The product was purified by fractional distillation (product 158°–166° C.). Yield 20.49 g (33%). Purity 90% by GC.

Perkin Elmer 8310 GC (8% carbowax+2% KOH on chromasorb 80–100 mesh, 80°–200° C. in 20 min. Product retention 5.775 minutes, allyl alcohol 3.61 min, bromoacetaldehyde dimethyl acetal 5.44 min. FID detection.

NMR 3.4 ppm 6H singlet —O$CH_3$, 3.5 ppm 2H doublet —$CH_2$—O—, 4.05 ppm doublet 2H —O—$CH_2$CH=, 4.5 ppm 1H triplet $CH$(—O$CH_3$)$_2$, 5.2 ppm 2H quartet —$CH_2$=CH—, 5.9 ppm 1H octet $CH_2$=$CH$.

Synthesis of 2-(methyloxyacetaldehyde dimethyl acetal) oxirane (II)

Compound (I) insert 15.53 g, $1.06 \times 10^{-1}$ mol was dissolved in dichloromethane (300 ml). meta-Chloroperbenzoic acid (Aldrich, 46.7 g, $2.71 \times 10^{-1}$ mol) was added and the solution was heated under reflux for approximately thirty hours. The solution was then cooled, washed (3×130 ml 1M NaOH, 2×50 ml brine) and dried over anhydrous magnesium sulphate. After filtration the solution was warmed and the dichloromethane removed under reduced pressure leaving the product as an oily residue. Yield 13.63 g (79.1%).

NMR 2.6 ppm 1H triplet, 2.8 ppm 1H triplet, 3.15 ppm 1H multiplet, 3.4 ppm 1H singlet —O$CH_3$, 3.45 ppm 1H doublet, 3.5 ppm 2H multiplet, 3.8 ppm 1H multiplet, 4.5 ppm 1H triplet —$CH$(—OMe)$_2$.

Synthesis of 1-(2-nitro-1-imidazolyl)-3-oxyacetaldehyde dimethyl acetal-propan-2-ol (III)

2-nitroimidazole (Aldrich, 3.06 g), potassium carbonate (0.23 g), Compound II insert (6.49 g) and ethanol (40 ml) were heated under reflux for six hours. The ethanol was then removed by rotary evaporation and the residue dissolved in ethylacetate (5 ml). Purification was achieved by passing the crude product solution through a silica column (approx. 450 ml bed volume) with petroleum spirit-ethyl acetate eluent (400 ml portions 25%, 50%, 75%, 100%×5 ethyl acetate). The purified product was in all five of the 100% ethylacetate fractions, which were combined and rotary evaporated to give a light yellow oil which crystallised on standing. Yield 7.2 g. Melting point 47°–49° C.

Synthesis of 2-(2-nitro-1-imidazolylmethyl)-1,4 -dioxane-6-ol (IV)

Compound III insert (4 g) was dissolved in tetrahydrofuran (50 ml). Hydrochloric acid (50 ml, 0.5M) was added and the solution was heated under reflux for one hour. The solution was cooled, extracted with ethylacetate (3×50 ml), dried over anhydrous magnesium sulphate, filtered and rotary evaporated to dryness. Yield 2.26 g.

Synthesis of 2-hydroxy-1-(2-nitro-1-imidazolyl)- 7,15,19-triaza-4-oxa-10,14,14,20,20 -pentamethyldocosane-13, 21-dione Dioxime (V) insert 1-amino-8,12-diaza-3,7,7,13,13 -pentamethylpentadecane-6,14-dione dioxime (XII) insert (200 mg, $5.6 \times 10^{-4}$ mol) was mixed with compound IV insert (280 mg, $1.22 \times 10^{-3}$ mol) in methanol (10 ml) plus acetic acid (8 drops) under an atmosphere of nitrogen. After 30 minutes sodium cyanoborohydride (Aldrich, 270 mg) was added and the solution was stirred overnight. Hydrochloric acid (50 ml, 0.5M) was added, then the mixture extracted with ethylacetate (2×60 ml). The pH of the aqueous layer was increased to pH 13.0 by addition of sodium hydroxide pellets, then the solution was extracted with dichloromethane (2×60 ml). The non-aqueous extracts were combined, washed with brine, dried over anhydrous magnesium sulphate and rotary evaporated to give a yellow oil. TLC analysis (silica gel fluorescent indicator. Eluent: dichloromethane, methanol, ammonia 10.3:0.2. UV detection and ninhydrin) showed a single spot at $R_f$ 0.5.

NMR 1.0 (3H, d), 1.25 (12H, s), 1.4–1.8 (7H, m), 1.85 (3H, s), 2.3 (2H, broad s), 2.5 (4H, m), 2.7–2.9 (4H, m), 3.5 (2H, m), 3.6 (2H, m), 4.1 (1H, broad s), 7.1 (1H, s), 7.5 (1H, s), 4.5 (1H, m), 9.7 (1H, m).

3-chloro-1-(2-nitroimidazolyl)propan-2-ol (VI) insert

Reference: Alden G. Beaman, William Tautz and Robert Duschinsky. Antimicrobial Agents, Chemother. 7 (520) 1968.

MP of product 155°–156° C. (Lit. 156°–158° C.). NMR (DMSO=$d_6$) 3.65 ppm multiplet 2 protons N—C$H_2$—CH—OH.

4 ppm, multiplet, one proton —$CH_2$—$CH$—$CH_2$ 4.3 and 4.7 ppm two multiplets, two protons $CH_2$—Cl 7.1 and 7.6 ppm, two proton singlets, HC=CH ring protons.

2-hydroxy-1-(2-nitroimidazolyl)-4,12,16-triaza- 7,11,11,17, 17-pentamethyl nonadecane-10,18-dione dioxime (VII) and N,N-bis[2-hydroxy-3-(2 -nitroimidazolyl)-propyl]-1-amino-8,12-diaza- 3,7,7,13,13-pentamethylpentadecane-6,14-dione dioxime (VIII) insert 1-amino-8,12-diaza-3,7,7,13,13-pentamethyl pentadecane-6-14-dione dioxime (XII 172 mg) insert was mixed with compound (VI) 102 m9 in 50% aqueous methanol (5 ml). The solution was stirred and warmed (50° C.) under an atmosphere of nitrogen for six hours. The crude reaction mixture was purified by HPLC (25×0.8 cm PRP column, Hamilton Laboratories, Solvent A 2% ammonia, Solvent B acetonitrile.

Gradient 10% B for 4 minutes then increased to 50% in 15 minutes, flow 3 ml min$^{-1}$ Detection at 325 nm. k'$_{(vii)}$=21, k'$_{(viii)}$=19.5). Solvent was removed by rotary evaporation. Yield VII—31 mg, Yield VIII=38 mg.

NMR (VII) insert 1.0 (3H, s), 1.25 (12H, s), 7.1 & 7.5 (2H, s), 1.3–1.6 (7H, m), 1.85 (3H, s), 2.3 (2H, m), 2.5 (4H, m), 2.7 (4H, m), 4.1 (1H, m), 4.3 (1H, m), 4.8 (1H, m).

NMR (VIII) insert 1.0 (3H, s), 1.25 (12H, s), 1.3–1.6 (7H, m), 1.85 (3H, s), 2.3 (2H, m), 2.5 (4H, m), 2.7 (6H, m), 4.1 (2H, m), 4.3 (2H, m), 4.7 (2H, m), 7.1–7.5 (2H, s).

Synthesis of 2,-hydroxy-1-(2-nitroimidazolyl)-4,9,13 -triaza-8,8,14,14-tetramethylhexadecane7,15-dione dioxime (IX) and N,N-bis[2-hydroxy-3-(2-nitro-1 -imidazolyl)-propyl-1-amino-5,9-diaza-4,4,10,10 -tetramethyldodecane-3, 11-dione dioxime (X) insert 1-amino-5,5-diazo-4,4,10,10 -tetramethyldodecane-3,11-dione dioxime (XI) insert. 150 mg was mixed with compound VI insert (100 mg) in 50% aqueous methanol (5 ml). The solution was stirred and warmed (50° C.) under an atmosphere of $N_2$ for eight hours. Purification was again achieved by HPLC. Yields (IX)=18 mg (X)=112 mg NMR MeOD (IX) 1.25 (12H, s), 1.6 (2H, t), 1.8 (3H, s), 2.4 (4Hm m), 2.55 (2H, t), 2.7 (1H, m), 2.85 (2H, m), 4.1 (1H, m), 4.3 (1H, m), 4.7 (1H, m).

NMR (X) 1.25 (12H, s), 1.5 (2H, m), 1.8 (3H, s), 2.4 (4H, m), 2.55 (4H, m), 2.7 (4H, m), 2.85 (2H, m), 4.1 (2H, m), 4.3 (2H, m), 4.85 (2H, m).

Synthesis of 1-amino-8-12-diaza-3,7,7,13, 13-pentamethyl pentadecane-6,14-dione dioxime (XII)

1. 2,2,2-trifluoroacetamide (Aldrich, 47 g) in DMF (150 ml) was added over a period of one hour to a stirred suspension of sodium hydride (Aldrich, 12.5 g) in DMF (100 mls) under an atmosphere of nitrogen. The reaction mixture was then allowed to stir for one hour.

Citronellol mesylate (3,7-dimethyl-oct-6 -ene-1-ol mesylate, 15.5 g) was added and the reaction mixture was heated at 80° C. for two hours. Heating was discontinued and the reaction mixture was left to stir overnight. Water was added to give a solution which was then rotary evaporated to a brown gum. This was taken up in water and extracted with diethyl ether. The ether extracts were dried with anhydrous magnesium sulphate, filtered and rotary evaporated to give a brown oil (weight 80 g). Purification of the desired product (N-trifluoroacetyl-1-amino-3,7-dimethyl-oct-6-ene-mesylate) was achieved on a silica column (petrol:ether 9:1) Yield 43 g.

2. N-trifluoroacetyl-3,7-dimethyl-oct-6-ene-1-ol mesylate (10 g) was mixed in pentane (100 ml) and cooled to –20° C. Nitrosyl chloride (2.76 mls) was added and the reaction mixture was stirred for 3 hours as it was permitted to warm to room temperature. The pentane was decanted off and the residue (a blue oil) was dried under reduced pressure.

Yield of N-trifluoroacetyl-7-chloro-3,7-dimethyl-6-nitroso-octylamine 11 g.

3. The product from above (11.5 g) was dissolved in acetonitrile (100 ml) and added over a period of 2½ hours to a mixture of N-(3-aminopropyl)-1-amino-1,1-dimethyl-2-butanone oxime (7.0 g) potassium bicarbonate (8 g) and acetonitrile. The mixture was then stirred for 3 days at room temperature. Approximately one-quarter of the reaction mixture was then worked up as follows:

Acetonitrile was removed under reduced pressure and the residue dissolved in water (≈50 ml), then acidified with hydrochloric acid to pH 2.0 and washed with diethyl ether. The aqueous solution was then basified to pH 12.0 and extracted with dichloromethane (3×50 ml). The non-aqueous extracts were combined and dried over anhydrous magnesium sulphate and concentrated to an oil under reduced pressure. Deprotection was effected by stirring the product in acetonitrile:2% ammonia solution for 1 week followed by removal of the solvent. The desired product was isolated by preparative HPLC as described in VII. Yield 2.4 g.

NMR ($^1$H, 500 MHz, CDCl$_3$): 1.0 (3H, d, CH—C$\underline{H}_3$), 1.25 (12H, s, CH$_3$), 1.4–1.7 (7H, m, —CH$_2$ and —C$\underline{H}$), 1.8 (3H s HON=C$\underline{H}_3$), 2.3 (2H, m, HON—CC$\underline{H}_2$), 2.4 (4H, m, NH—C$\underline{H}_2$), 2.7 (2H, m, NH$_2$—CH$_2$).

Synthesis of 1-amino-4,4,10,10-tetramethyl-5-9-diazododecane-3,11-dione-dioxime (XI)

Preparation of N-trifluoroacetyl-4-methyl-2-pentenamine

Trifluoroacetamide (11.0 g, 97 mmol) dimethylformamide (50 ml) was added dropwise with stirring to a suspension of sodium hydride (2.33 g, 97 mmol), 2.91 g of a 80% dispersion in oil prewashed with dry pet. ether 40°–60° C. in dimethylformamide (50 ml) at 20° C. under nitrogen. After 1 hr 5-bromo-2-methyl-2-pentene (13.2 g, 81 mmol) dissolved in dimethylformamide (20 ml) was added and the mixture stirred at 70° C. for 18 hours. The solvent was then removed under reduced pressure to give a brown oil, to which was added water and the product extracted with ether (x3). The ethereal layers were combined and then dried with magnesium sulphate before concentrating to a brown oil. Product purification was then carried out by flash chromatography using a gradient elution from ether:pet.ether 40°–60° C. 5:95 to ether:pet.ether 40°–60° C. 25:75 to yield 0.63 g (3%) of N,N-(4-methyl-2-penten)trifluroacetamide followed by 7.73 g (49%) of N-trifluoroacetyl-4-methyl-2-pentenamine. B.p. 84° C. 1.3 mm Hg, NMR ($^1$H, 60 MHz, CDCl$_3$): 6.6 6.1 (1H bs, N$\underline{H}$), 5.1 (1H, m, C=C$\underline{H}$), 3.35 (2H, q, C$\underline{H}_2$NH), 2.25 (2H, q C$\underline{H}_2$CH$_2$N), 1.7 (3H, s, C $\underline{H}_3$C=C), 1.6 (3H, s, CH$_3$C=C).

Preparation of N-trifluoroacetyl-4-chloro-4-methyl-3-nitroso-pentylamine

To N-trifluoroacetyl-4-methyl-2-pentenamine (2.07 g, 10.6 mmol) dissolved in n-hexane (20 ml) at –15° C. was added a precondensed quantity of nitrosylchloride (0.9 ml, 1.26 g, 19.2 mmol). The reaction was maintained at –15° C. for 30 mins and then allowed to warm to room temperature and then stirred for a further 4 hours. The product precipitated out of solution and was subsequently filtered off and washed with n-hexane before drying under high vacuum to give 2.19 g (79%) of a pale blue solid. M.p. 91°–93° C.

Preparation of 1-amino-4,4,10,10-tetramethyl-5,9-diazododecane-3,11-dione-dioxime (XI) insert To N-(3-aminopropyl)-1-amino-1,1-dimethyl-2-butanone oxime (3.68 g, 21.3 mmol) dissolved in acetonitrile (100 ml) was added potassium bicarbonate (4.0 g, 40 mmol) followed by a dropwise addition of N-trifluoroacetyl-4-chloro-4-methyl-3-nitroso-pentylamine (6.16 g, 23.6 mmol) dissolved in acetonitrile (100 ml). The reaction mixture was then stirred at room temperature for two days. The solvent was then removed under reduced pressure and the residue taken up in water. The pH of the aqueous solution was taken to pH 2 with hydrochloric acid and was washed with ether. The trifluoroacetyl derivative of the product could then be isolated by adjusting the pH of the aqueous solution to pH 12 with sodium hydroxide solution followed by extraction with dichloromethane (x4). The dichloromethane extracts were then combined and dried with MgSO$_4$ before finally concentrating to a foam. The trifluoromethyl protecting group was then removed by standing the product in 0.4M NH$_3$(aq.) solution for 7 days followed by the removal of the solvent. The desired product was purified by preparative reverse phase HPLC using a PRP preparative column. Detection was via a variable wavelength u.v. detector set at 210 nm and the solvent system was a mixture of acetonitrile and 0.4M NH$_3$(aq.) at a flow rate of 10 ml min$^{-1}$. The crude product was dissolved to a concentration of 200 mg ml$^{-1}$ in water and up to 600 mg applied to the HPLC column at any one time.

After HPLC purification 1.3 g (20%) of the product was isolated as a gum.

NMR (1H, 500 MHz, CDCl$_3$): 2.97 (2H, m, C$\underline{H}_2$NH$_2$), 2.60 (2H, m, HON=CC$\underline{H}_2$), 2.53 (2H, t, HN—C$\underline{H}_2$), 2.47 (2H, t, HNC$\underline{H}_2$, 1.86 (3H, s, HON=CC$\underline{H}_3$), 1.61 (2H, m, H$_2$C$\underline{H}_2$), 1.25 (12H, s, C$\underline{H}_3$).

References

1. Harland, P. A., Hodge, P., Mayghan, W., Wildsmith E., Synthesis, 1984, 961.

2. Canning, L. R., Nowotnik, D. P., British Pat. Appl. 842684.5.

EXAMPLE 6

$^{99M}$Tc-Labelling of Test Compounds V, VII, VIII, IX, X

Samples of each test ligand (1 mg) were aliquoted into N$_2$-filled vials (10 ml capacity) fitted with butyl rubber closures and metal overseals. Sodium bicarbonate solution (1 ml, 0.1M, deoxygenated with a stream of N$_2$ for 20 minutes) was added through the rubber closures with a hypodermic syringe. After 5–10 minutes stannous chloride was added (Sigma, 5 mg SnCl$_2$ in 250 ml of N$_2$-purged saline, filtered through an 0.22 micron filter, 1 ml per vial): this was immediately followed with $^{99m}$Tc-sodium pertechnetate solution (100–200 μl, 0.2–0.4 GBq). The solution was incubated at ambient temperature for 30 minutes and was ready for rise.

EXAMPLE 7

Chinese hamster V79 379A fibroblasts in suspension in vitro were used as the test system, gassed with air/5% $CO_2$ (oxic) or nitrogen/5% $CO_2$ (hypoxic). This is a test system very widely used in assessing hypoxia-induced binding or bioreductive drugs. Tc-99m labelled compounds were added at concentrations which are likely to be clinically achievable (up to about 50 μmol $dm^{-3}$).

V79 379A Chinese hamster cells were harvested from exponential suspension culture and resuspended at $1.1 \times 10^6$ cells cm in Eagle's minimum essential medium with 7.5% foetal calf serum. Cells (20 $cm^3$) were transferred to small spinner vessels and gassed with either air/5% (oxic) or nitrogen/5% $CO_2$ (hypoxic) at 37° C. After 30 minutes, between 0.5 $cm^3$ and 1 $cm^3$ of Tc-99m labelled compound was added. At timed intervals, 1 $cm^3$ of cell suspension was withdrawn from each flask and chilled on ice in small polystyrene centrifuge tubes. The cells were centrifuged and washed three times in ice-cold medium (Eagle's minimum essential medium) to give constant counts in the cell pellet. The pellets were counted in an LKB 1282 Compugamma counter. The initial supernatant was diluted 1 in 100 with saline and 1 $cm^3$ was counted. All samples were counted at the end of the incubation period and counts have been corrected for decay during counting but not for decay during incubation.

Attempts were made to decrease the amount of non-specific binding by incubating the cell samples in a large volume of medium for one hour at 37° C. under oxic conditions. Although this treatment reduced the total counts in both hypoxic and oxic cell pellets, it did not improve the differential.

Results

Five nitroimidazoles labelled with Tc-99m were evaluated. The table below shows the hypoxic/oxic ratio after five hours' incubation. All five Tc-99m labelled nitroimidazoles gave a significant differential binding, in the range 1.6–6.4.

| Compound | Type | Hypoxic:oxic ratio at 5 h | Notes |
|---|---|---|---|
| IX | nitro | 2.6 | |
| X | nitro | 1.6 | possible colloid formation? |
| VII | nitro | 4.1 | |
| VIII | nitro | 3.3 | |
| V | nitro | 6.4 | |

In some cases the agents are only soluble with difficulty, and this appeared to cause precipitation onto cells giving less discrimination between oxic and hypoxic states.

We claim:

1. A complex of a ligand consisting of a least one quinone, triazole or aromatic nitro compound bonded to a metal chelating moiety, which is a his-amine oxime of the formula

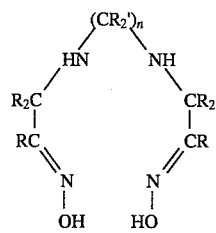

where n=0–3, through at least one R, and wherein R and R' are the same or different and each is H; hydrocarbyl; amino; amido; hydroxy; alkoxy; alkoxyalkyl; or carboxylic acid; and which are unsubstituted or substituted with a hydrophilic group selected from the group consisting of amino, amido or hydroxy, and a metal atom chelated by the metal chelating moiety, wherein the metal is selected from the group consisting of $^{99m}Tc$, $^{186}Re$, $^{188}Re$, $^{67}Cu$ and $^{107}Ag$.

2. The complex as claimed in claim 1, wherein the aromatic nitro compound is a 2-nitroimidazole.

3. The complex as claimed in claim 2, wherein the 2-nitroimidazole is misonidazole.

4. The complex as claimed in claim 1, wherein the ligand is selected from those designated

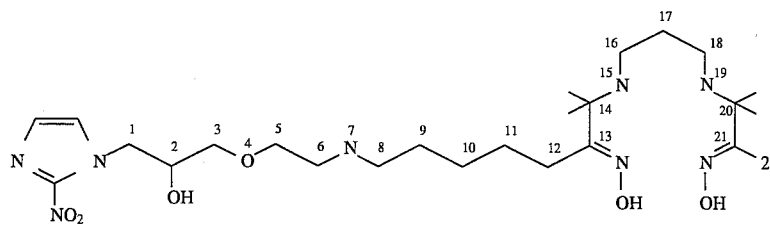

V

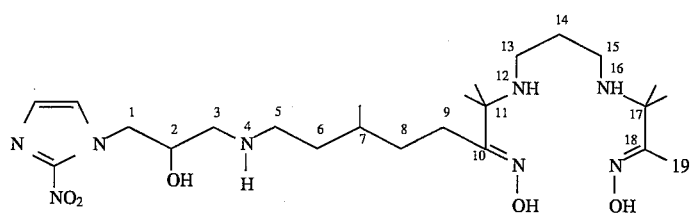

VII

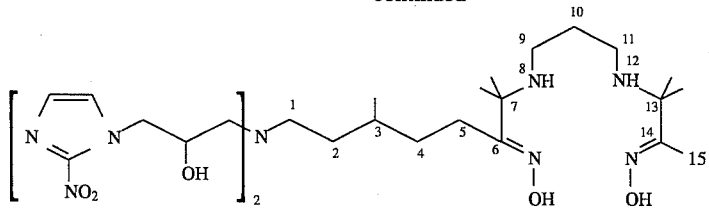

VIII

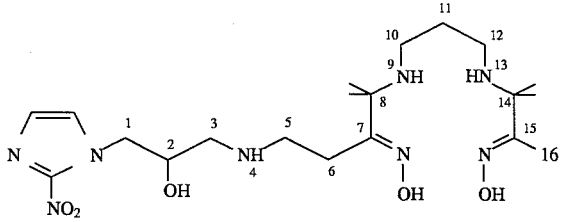

IX

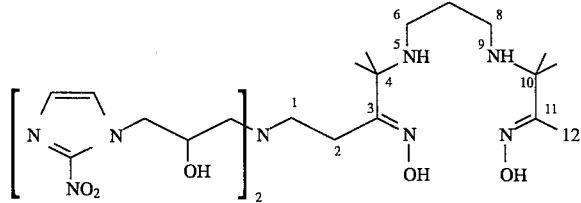

X

5. The complex as claimed in claim 4 wherein the ligand is 2-hydroxy-1-(2-nitro-1-imidazolyl)-7,15,19-triaza-4-oxa-10,14,14,20,20-pentamethyldocosane-13,21-dione dioxime.

6. The complex as claimed in claim 1, wherein the hydrocarbyl is alkyl, aryl or cycloalkyl and the hydrophilic group is hydroxy.

7. The complex as claimed in claim 1, having the structure Q-A-L-M or (Q-A)$_2$-L-M, where Q is the quinone, triazole or aromatic nitro compound, A is a linking group, L is the metal chelating moiety and M is the metal.

8. The complex as claimed in claim 7, wherein the linking group A is a chain from 1 to 12 atoms long.

9. The complex as claimed in claim 7, wherein Q is 2-nitroimidazole L is a propylene-1,3-bis-amine oxime and M is Technetium-99m.

* * * * *

UNITED STATES PATENT AND TRADEMARK OFFICE
CERTIFICATE OF CORRECTION

PATENT NO. : 5,506,345
DATED : April 9, 1996
INVENTOR(S) : Anthony L. RILEY et al.

It is certified that error appears in the above-indentified patent and that said Letters Patent is hereby corrected as shown below:

Col. 12, lines 19-28,

Claim 1, please replace the formula in line 4 with the following formula:

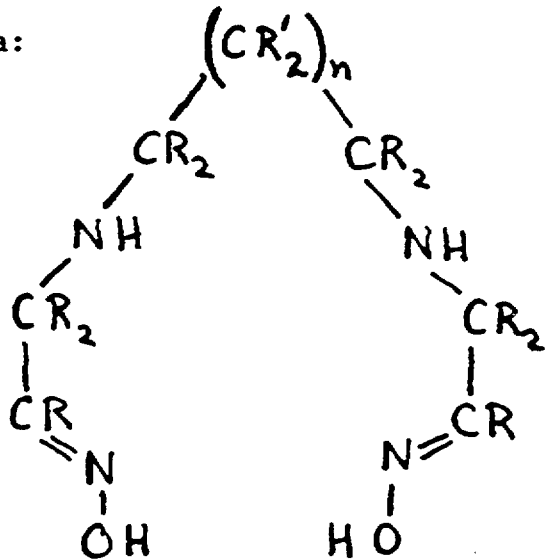

Signed and Sealed this

Twentieth Day of August, 1996

Attest:

BRUCE LEHMAN

Attesting Officer          Commissioner of Patents and Trademarks